United States Patent
Mori et al.

(10) Patent No.: US 6,803,489 B2
(45) Date of Patent: Oct. 12, 2004

(54) PURIFICATION PROCESS OF FLUORENYLIDENEDIALLYLPHENOL

(75) Inventors: Hiroaki Mori, Tokyo (JP); Shigeki Inatomi, Nobeoka (JP)

(73) Assignee: JFE Chemical Corporation, Tokyo (JP)

(*) Notice: Subject to any disclaimer, the term of this patent is extended or adjusted under 35 U.S.C. 154(b) by 0 days.

(21) Appl. No.: 10/684,483

(22) Filed: Oct. 15, 2003

(65) Prior Publication Data

US 2004/0082819 A1 Apr. 29, 2004

(30) Foreign Application Priority Data

Oct. 17, 2002 (JP) ........................................ 2002-303564

(51) Int. Cl.$^7$ .............................................. C07C 39/12
(52) U.S. Cl. ...................................................... 568/719
(58) Field of Search ......................................... 568/719

(56) References Cited

U.S. PATENT DOCUMENTS 4,981,934 A * 1/1991 Stenzenberger et al. .... 526/262

* cited by examiner

Primary Examiner—Michael L. Shippen
(74) Attorney, Agent, or Firm—Oblon, Spivak, McClelland, Maier & Neustadt, P.C.

(57) ABSTRACT

A process is provided for the purification of 4,4'-(9-fluorenylidene)diallylphenol. With an inclusion-compound-forming solvent which contains an inclusion-compound-forming compound capable of forming an inclusion compound with 4,4'-(9-fluorenylidene)diallylphenol, crude 4,4'-(9-fluorenylidene)diallylphenol is dissolved to form the inclusion compound in the form of a solution. The inclusion compound is then caused to deposit, for example, by charging the solution of the inclusion compound into a poor solvent for the inclusion compound, for example, an aliphatic hydrocarbon solvent such as n-hexane, n-heptane, cyclohexane or a mixture thereof.

12 Claims, No Drawings

PURIFICATION PROCESS OF FLUORENYLIDENEDIALLYLPHENOL

FIELD OF THE INVENTION

This invention relates to a purification process of 4,4'-(9-fluorenylidene)diallylphenol.

DESCRIPTION OF THE BACKGROUND 4,4'-(9-Fluorenylidene)diallylphenol is useful as a raw material for polyesters and polyamides, and is known to permit construction of polymers, that develop optical, mechanical or various other functional characteristics, by introduction of its fluorene skeleton into polymer skeletons or by use of one or both of the allyl groups contained in its structure. As a process for the production of 4,4'-(9-fluorenylidene)diallylphenol, the process disclosed in JP 10-77338 A is known.

4,4'-(9-Fluorenylidene)diallylphenol is, therefore, expected to find utility as a raw material for functional polymers, and is desired to be supplied as a high-purity product. Due to its low crystallizability, however, it has heretofore been difficult to efficiently obtain 4,4'-(9-fluorenylidene)diallylphenol with sufficient purity.

SUMMARY OF THE INVENTION

An object of the present invention is, therefore, to provide an industrially advantageous process for the purification of 4,4'-(9-fluorenylidene)diallylphenol which is useful as a raw material for functional polymers.

The above-described object can be achieved by the present invention to be described hereinafter. Described specifically, the present invention provides a process for the purification of 4,4'-(9-fluorenylidene)diallylphenol. The purification process includes dissolving crude 4,4'-(9-fluorenylidene)diallylphenol with an inclusion-compound-forming solvent, which comprises an inclusion-compound-forming compound capable of forming an inclusion-compound with 4,4'-(9-fluorenylidene)diallylphenol, to form the inclusion compound in a form of a solution, and then causing the inclusion compound to deposit.

In the present invention, 4,4'-(9-fluorenylidene)diallylphenol is represented by the following structural formula:

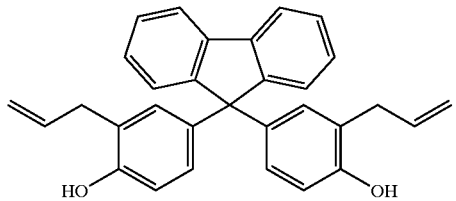

According to the purification process of the present invention, 4,4'-(9-fluorenylidene)diallylphenol can be easily produced with high purity on an industrial scale although its purification and recovery have been difficult to date.

4,4'-(9-Fluorenylidene)diallylphenol purified as described above is useful, for example, as a raw material for polyesters and polyamides. By introduction of its fluorene skeleton into polymer skeletons, it is possible to obtain polymers which develop optical, mechanical or various other functional characteristics. Construction of polymers is also feasible by making use of one or both of the allyl groups in its structure. The present invention can, therefore, impart a still wider variety of functional characteristics to polymers.

DETAILED DESCRIPTION OF THE PREFERRED EMBODIMENTS

The present invention will hereinafter be described in further detail based on preferred embodiments.

As processes for the production of 4,4'-(9-fluorenylidene)diallylphenol, to which the present invention is applied, the following first and second processes can be mentioned. According to the first process, 4,4'-(9-fluorenylidene)diallylphenol is synthesized from fluorenone and o-allylphenol in the presence of an acid catalyst, and by a conventional purification method such as distillation under reduced pressure, the acid catalyst and excess o-allylphenol are then removed from the reaction mixture to obtain crude 4,4'-(9-fluorenylidene)diallylphenol.

According to the second process, an allyl halide is caused to act on 4,4'-(9-fluorenylidene)diphenol in the presence of a base compound to effect diallyl-etherification, and then, the Claisen rearrangement is conducted to obtain crude 4,4'-(9-fluorenylidene)diallylphenol.

In the first process, the reaction product obtained as described above contains inter alia the below-described compound I and compound II. In the second process, on the other hand, the reaction product obtained as described above contains inter alia a solvent, which was employed in the Claisen rearrangement, and as a byproduct, the below-described compound III. Crude 4,4'-(9-fluorenylidene)diallylphenol with such byproduct or byproducts contained therein generally has 80 to 90% purity.

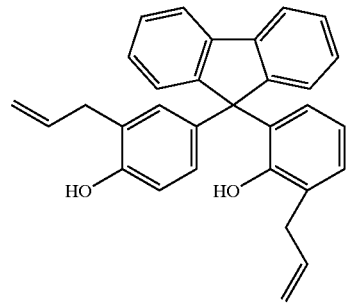

Compound I

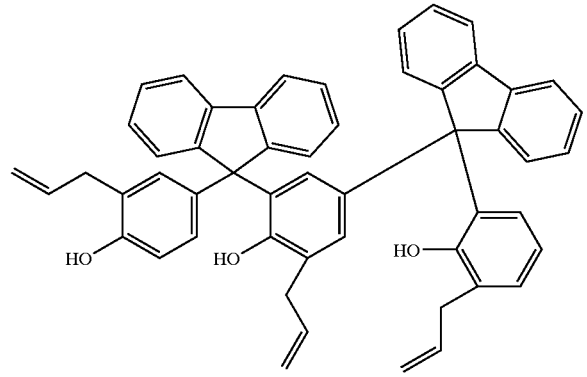

Compound II

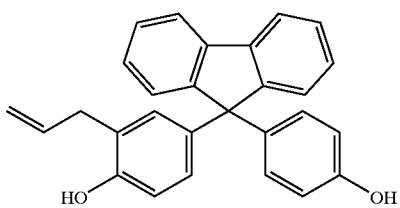

Compound III

Purification and recovery of the above-described crude 4,4'-(9-fluorenylidene)diallylphenol can be conducted as will be described hereinafter. Firstly, crude 4,4'-(9-fluorenylidene)diallylphenol is dissolved in a solvent which contains an inclusion-compound-forming compound capable of forming an inclusion compound with 4,4'-(9-fluorenylidene)-diallylphenol. Upon this dissolution, it is preferred that the inclusion-compound-forming compound also serves as the inclusion-compound-forming solvent. It is, however, possible to use the inclusion-compound-forming compound in combination with an appropriate amount of another solvent.

The inclusion-compound-forming compound is generally a polar solvent, which can also serve as a solvent upon formation of 4,4'-(9-fluorenylidene)diallylphenol into the inclusion compound. Specific examples of the inclusion-compound-forming compound can include carbonyl compounds such as acetone, methyl ethyl ketone, methyl isobutyl ketone; alcohols such as isopropyl alcohol and butanol; nitrile compounds such as acetonitrile and benzonitrile; ethers such as tetrahydrofuran, dioxane and diisopropyl ether; carboxylic acids such as acetic acid and propionic acid; amines such as pyridine and aniline; phenols such as phenol and cresol; acetate esters such as methyl acetate, ethyl acetate and isopropyl acetate; organic halogenides such as dichloroethane, dichloromethane and chlorobenzene; all the inclusion-compound-forming compounds (polar solvents) each of which can form an inclusion compound with 4,4'-(9-fluorenylidene)diallylphenol, and mixtures thereof.

In the inclusion-compound-forming solvent with the inclusion-compound-forming compound contained therein, crude 4,4'-(9-fluorenylidene) diallylphenol can be dissolved at 20 to 200° C., preferably 50 to 120° C. A dissolution temperature lower than the above-described temperature range leads to a reduction in the solubility of crude 4,4'-(9-fluorenylidene)-diallylphenol and requires labor for the dissolution. A dissolution temperature higher than the above-described temperature range, on the other hand, induces elimination of the allyl groups. Dissolution temperatures outside the above-described temperature range are therefore not preferred. The inclusion-compound-forming compound (for example, a polar solvent) can be used 0.5 to 5 times by weight, preferably 0.7 to 2 times by weight as much as crude 4,4'-(9-fluorenylidene)diallylphenol.

Next, the inclusion compound between 4,4'-(9-fluorenylidene)diallylphenol and the inclusion-compound-forming compound is caused to deposit. As an illustrative convenient method, a description will herein after be made of a method in which a solution of the inclusion compound is charged into a solvent which is a poor solvent for the inclusion compound. The solution of the inclusion compound is added dropwise into an aliphatic hydrocarbon solvent which is a poor solvent. Usable examples of the aliphatic hydrocarbon solvent can include n-hexane, n-heptane, cyclohexane, petroleum ether and mixtures thereof. The aliphatic hydrocarbon solvent can be used 1 to 20 times by weight, preferably 3 to 10 times by weight as much as the solution of the inclusion compound. Subsequent to completion of the dropwise addition of the solution of the inclusion compound, the resulting mixture is stirred for 1 to 3 hours or so to ensure deposition (or crystallization) of the inclusion compound.

Except for the inclusion-compound-forming compound included in the inclusion compound, the inclusion compound so deposited has been purified to sufficient level. If the inclusion-compound-forming compound included in the inclusion compound does not interfere with the subsequent step, the inclusion compound obtained as described above may be supplied, as is, as a raw material for the subsequent step. As an alternative, the inclusion-compound-forming compound (for example, a polar solvent) maybe removed by the below-exemplified method such that the inclusion compound can be supplied as product free of the inclusion-compound-forming compound. For example, the deposited inclusion compound is further dissolved in a solvent. The dissolution temperature at this time can range from 0 to 200° C., preferably from 20 to 100° C. Dissolution at a temperature higher than 200° C. induces elimination of the allyl groups from 4,4'-(9-fluorenylidene)diallylphenol, and therefore, is not preferred.

The solution of the inclusion compound is then heated such that the included, inclusion-compound-forming compound is distilled off. To allow smooth elimination of the inclusion-compound-forming compound by distillation, the distillation can be conducted under reduced pressure such that the inclusion-compound-forming compound is distilled off along with a portion of the solvent employed for the dissolution. After the elimination of the inclusion-compound-forming compound by distillation, the solvent employed for the dissolution may be completely distilled off to obtain 4,4'-(9-fluorenylidene)diallylphenol in the form of a solid product. As an alternative, a solvent usable in the subsequent step may be chosen as a solvent for use in the dissolution (herein after called "the inclusion-compound-forming solvent") Subsequent to elimination of the inclusion-compound-forming compound, the solution may be adjusted to an appropriate concentration and may then be supplied, as is, in the form of the solution to the subsequent step.

As the inclusion-compound-dissolving solvent, a compound incapable of forming an inclusion compound with 4,4'-(9-fluorenylidene)diallylphenol, in other words, a solvent other than those exemplified above as the inclusion-compound-forming compound can be used. Illustrative of the inclusion-compound-dissolving solvent are aromatic hydrocarbon solvents such as toluene, benzene, xylene, mesitylene, tetralin, methylnaphthalene, and mixtures thereof. The inclusion-compound-dissolving solvent can be used preferably in an amount 0.5 to 50 times by weight as much as the inclusion compound.

By the purification process of the present invention as described above, high-quality (in other words, high-purity) 4,4'-(9-fluorenylidene)diallylphenol can be easily obtained with high recovery rate without needing special industrial facilities.

EXAMPLES

The present invention will next be described more specifically on the basis of Examples. It should, however, be borne in mind that the present invention is by no means limited by the following Examples.

Example 1

Crude 4,4'-(9-fluorenylidene)diallylphenol (50 g) of 83.3% purity (HPLC data) was maintained as a raw material at 60° C., into which acetone (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the acetone inclusion compound of the crude 4,4'-(9-fluorenylidene)-diallylphenol.

Toluene in an amount 12 times by weight as much as the inclusion compound was added at room temperature to dissolve the inclusion compound so that a solution of 4,4'-(9-fluorenylidene)diallylphenol in toluene was obtained. The solution was heated to 100° C., at which distillation was conducted under reduced pressure until the amount of a distillate reached 200 mL. As a result of an analysis of the resultant toluene solution by gas chromatography, complete elimination of acetone was ascertained. Under reduced pressure, toluene was completely distilled off to recover 4,4'-(9-fluorenylidene)diallylphenol in a solid form. As a result of an analysis by HPLC, the purity of the 4,4'-(9-fluorenylidene)diallylphenol was found to be 98.3%. Accordingly, its recovery rate from the crude 4,4'-(9-fluorenylidene)diallylphenol was 81.6%.

Example 2

Crude 4,4'-(9-fluorenylidene)diallylphenol (50 g) of 83.3% purity (HPLC data) was maintained as a raw material at 60° C., into which 1-butanol (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the 1-butanol inclusion compound of the crude 4,4'-(9-fluorenylidene)-diallylphenol.

Toluene in an amount 12 times by weight as much as the inclusion compound was added at room temperature to dissolve the inclusion compound so that a solution of 4,4'-(9-fluorenylidene)diallylphenol in toluene was obtained. The solution was heated to 100° C., at which distillation was conducted under reduced pressure until the amount of a distillate reached 200 mL. As a result of an analysis of the resultant toluene solution by gas chromatography, complete elimination of 1-butanol was ascertained. Under reduced pressure, toluene was completely distilled off to recover 4,4'-(9-fluorenylidene) diallylphenol in a solid form. As a result of an analysis by HPLC, the purity of the 4,4'-(9-fluorenylidene)diallylphenol was found to be 98.2%. Accordingly, its recovery rate from the crude 4,4'-(9-fluorenylidene)diallylphenol was 78.6%.

Example 3

Crude 4,4'-(9-fluorenylidene)diallylphenol (50 g) of 83.3% purity (HPLC data) was maintained as a raw material at 60° C., into which tetrahydrofuran (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the tetrahydrofuran inclusion compound of the crude 4,4'-(9-fluorenylidene)-diallylphenol.

Toluene in an amount 12 times by weight as much as the inclusion compound was added at room temperature to dissolve the inclusion compound so that a solution of 4,4'-(9-fluorenylidene)diallylphenol in toluene was obtained. The solution was heated to 100° C., at which distillation was conducted under reduced pressure until the amount of a distillate reached 200 mL. As a result of an analysis of the resultant toluene solution by gas chromatography, complete elimination of tetrahydrofuran was ascertained. Under reduced pressure, toluene was completely distilled off to recover 4,4'-(9-fluorenylidene) diallylphenol in a solid form. As a result of an analysis by HPLC, the purity of the 4,4'-(9-fluorenylidene)diallylphenol was found to be 98.3%. Accordingly, its recovery rate from the crude 4,4'-(9-fluorenylidene)diallylphenol was 84.6%.

Example 4

Crude 4,4'-(9-fluorenylidene)diallylphenol (50 g) of 83.2% purity (HPLC data) was maintained as a raw material at 60° C., into which phenol (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the phenol inclusion compound of the crude 4,4'-(9-fluorenylidene)-diallylphenol.

Toluene in an amount 12 times by weight as much as the inclusion compound was added at room temperature to dissolve the inclusion compound so that a solution of 4,4'-(9-fluorenylidene)diallylphenol in toluene was obtained. The solution was heated to 100° C., at which distillation was conducted under reduced pressure until the amount of a distillate reached 200 mL. As a result of an analysis of the resultant toluene solution by gas chromatography, complete elimination of phenol was ascertained. Under reduced pressure, toluene was completely distilled off to recover 4,4'-(9-fluorenylidene)diallylphenol in a solid form. As a result of an analysis by HPLC, the purity of the 4,4'-(9-fluorenylidene)diallylphenol was found to be 98.2%. Accordingly, its recovery rate from the crude 4,4'-(9-fluorenylidene)diallylphenol was 80.6%.

Example 5

Crude 4,4'-(9-fluorenylidene)diallylphenol (50 g) of 83.2% purity (HPLC data) was maintained as a raw material at 60° C., into which pyridine (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the pyridine inclusion compound of the crude 4,4'-(9-fluorenylidene)-diallylphenol.

Toluene in an amount 12 times by weight as much as the inclusion compound was added at room temperature to dissolve the inclusion compound so that a solution of 4,4'-(9-fluorenylidene)diallylphenol in toluene was obtained. The solution was heated to 100° C., at which distillation was conducted under reduced pressure until the amount of a distillate reached 200 mL. As a result of an analysis of the resultant toluene solution by gas chromatography, complete elimination of pyridine was ascertained. Under reduced pressure, toluene was completely distilled off to recover 4,4'-(9-fluorenylidene) diallylphenol in a solid form. As a result of an analysis by HPLC, the purity of the 4,4'-(9-fluorenylidene)diallylphenol was found to be 98.2%. Accordingly, its recovery rate from the crude 4,4'-(9-fluorenylidene)diallylphenol was 75.6%.

Example 6

Crude4,4'-(9-fluorenylidene)diallylphenol (50 g) of 83.3% purity (HPLC data) was maintained as a raw material at 60° C., into which acetone (50 g) was added to prepare a homogeneous solution. The solution was allowed to cool down to room temperature, and was then charged into n-hexane (500 g) over about 1 hour. At the same temperature the resulting mixture was stirred for 1 hour, and an inclusion compound formed as a deposit was collected by filtration. The inclusion compound was washed with n-hexane (30 g) to afford the acetone inclusion compound of the crude 4,4'-(9-fluorenylidene)-diallylphenol.

N,N-Dimethylformamide in an amount 5 times by weight as much as the inclusion compound was added at room temperature to dissolve the inclusion compound so that a solution of 4,4'-(9-fluorenylidene)diallylphenol in N,N-dimethylformamide was obtained. The solution was heated to 100° C., at which distillation was conducted under reduced pressure until the amount of a distillate reached 200 mL. As a result of an analysis of the resultant N,N-dimethylformamide solution by gas chromatography, complete elimination of acetone was ascertained. Under reduced pressure, toluene was completely distilled off to recover 4,4'-(9-fluorenylidene)diallylphenol in a solid form. As a result of an analysis by HPLC, the purity of the 4,4'-(9-fluorenylidene)diallylphenol was found to be 98.3%. Accordingly, its recovery rate from the crude, 4,4'-(9-fluorenylidene)diallylphenol was 81.6%.

This application claims the priority of Japanese Patent Application 2002-303564 filed Oct. 17, 2002, which is incorporated herein by reference.

What is claimed is:

1. A process for the purification of 4,4'-(9-fluorenylidene) diallylphenol, which comprises dissolving crude 4,4'-(9-fluorenylidene)diallylphenol with an inclusion-compound-forming solvent, which comprises an inclusion-compound-forming compound capable of forming an inclusion compound with 4,4'-(9-fluorenylidene)diallylphenol, to form said inclusion compound in a form of a solution, and then causing said inclusion compound to deposit.

2. The process of claim 1, wherein said inclusion compound is caused to deposit by charging said solution of said inclusion compound into a poor solvent for said inclusion compound.

3. The process of claim 2, wherein said poor solvent is an aliphatic hydrocarbon solvent.

4. The process of claim 3, wherein said aliphatic hydrocarbon solvent is selected from the group consisting of n-hexane, n-heptane, cyclohexane, petroleum ether and mixtures thereof.

5. The process of claim 1, further comprising dissolving said deposited inclusion compound in an inclusion-compound-dissolving solvent, and then distilling off said inclusion-compound-forming compound along with a portion of said inclusion-compound-dissolving solvent to obtain 4,4'-(9-fluorenylidene)diallylphenol in a form free of said inclusion-compound-forming compound.

6. The process of claim 5, wherein said distillation is conducted such that 4,4'-(9-fluorenylidene)diallylphenol is obtained in a form of a solution dissolved in said inclusion-compound-dissolving solvent.

7. The process of claim 5, wherein said inclusion-compound-dissolving solvent is a solvent incapable of forming an inclusion compound with 4,4'-(9-fluorenylidene)-diallylphenol.

8. The process of claim 7, wherein said inclusion-compound-dissolving solvent is selected from the group consisting of toluene, benzene, xylene, mesitylene, tetralin, methylnaphthalene, and mixtures thereof.

9. The process of claim 1, wherein said inclusion-compound-forming compound and said inclusion-compound-forming solvent are the same.

10. The process of claim 9, wherein a polar solvent is used as said inclusion-compound-forming compound and said inclusion-compound-forming solvent.

11. The process of claim 10, wherein said polar solvent is selected from the group consisting of carbonyl compounds, alcohols, nitriles, ethers, carboxylic acids, amines, phenols, acetate esters, organic halogenides, and mixtures thereof.

12. The process of claim 10, wherein said polar solvent is selected from the group consisting of acetone, methyl ethyl ketone, methyl isobutyl ketone, isopropyl alcohol, butanol, acetonitrile, benzonitrile, tetrahydrofuran, dioxane, diisopropyl ether, acetic acid, propionic acid, pyridine, aniline, phenol, cresol, methyl acetate, ethyl acetate, isopropyl acetate, dichloroethane, dichloromethane, chlorobenzene, and mixtures thereof.

* * * * *